United States Patent
Kang et al.

(10) Patent No.: US 7,147,874 B2
(45) Date of Patent: Dec. 12, 2006

(54) PHARMACEUTICAL COMPOSITION FOR PREVENTION AND TREATMENT OF PREMATURE EJACULATION AND/OR HYPERSENSITIVITY OF SEXUAL STIMULATION

(75) Inventors: Jin-ah Kang, Yongin (KR); Tae-jin Ham, Seoul (KR); Hee-chol Kang, Daejeon (KR); Hi-jae Cho, Seongnam (KR); Young-hoon Kim, Seoul (KR); Seong-hak Jeong, Seoul (KR)

(73) Assignee: CJ Corp. (KR)

( * ) Notice: Subject to any disclaimer, the term of this patent is extended or adjusted under 35 U.S.C. 154(b) by 0 days.

(21) Appl. No.: 10/328,301

(22) Filed: Dec. 23, 2002

(65) Prior Publication Data
US 2003/0152650 A1    Aug. 14, 2003

(30) Foreign Application Priority Data
Dec. 21, 2001    (KR) ............... 10-2001-0082978

(51) Int. Cl.
*A61K 36/258*    (2006.01)
*A61K 36/00*    (2006.01)

(52) U.S. Cl. ............... 424/728; 424/725

(58) Field of Classification Search ........... 424/195.1, 424/725, 728
See application file for complete search history.

(56) References Cited

U.S. PATENT DOCUMENTS 4,746,509 A * 5/1988 Haggiage et al. ......... 424/449
5,587,167 A * 12/1996 Choi et al. ............... 424/728
6,726,935 B1 * 4/2004 Ji et al. .................... 424/537

FOREIGN PATENT DOCUMENTS

KR    P148511    4/1995
WO    WO 0147539    7/2001

OTHER PUBLICATIONS

Revilla et al. Comparison of Several Procedures Used for the Extraction of Anthocyanins From Red Grapes; J. Agric. Food Chem. 1998, 46, 4592-4597.*

Database Druglaunch 'Online!; Drug Launches, Mar. 22, 1993; Kwang Dong Korea: "Trade name: Young Shim"; retrieved from STN; Database accession No. 94: 48879, XP002235561—*abstract*.

European Search Report—COMMUNICATION for Application No. EP 02 25 8901—Mar. 21, 2003.

* cited by examiner

*Primary Examiner*—Patricia Leith
(74) *Attorney, Agent, or Firm*—Cantor Colburn LLP

(57) ABSTRACT

A pharmaceutical composition for the prevention and treatment of premature ejaculation and/or hypersensitivity of sexual stimulation is provided. The composition contains purified sumsoo extract and purified ginseng extract containing saponin as the main component, without other herbal essential oil components.

5 Claims, 1 Drawing Sheet

PHARMACEUTICAL COMPOSITION FOR PREVENTION AND TREATMENT OF PREMATURE EJACULATION AND/OR HYPERSENSITIVITY OF SEXUAL STIMULATION

TECHNICAL FIELD

The present invention relates to a pharmaceutical composition for the prevention and treatment of premature ejaculation and/or hypersensitivity of sexual stimulation.

BACKGROUND ART

Hypersensitivity of sexual stimulation is known to be caused generally due to a disorder in the complex cooperation between the peripheral nervous system and the central nervous system. Hypersensitivity of sexual stimulation is known to lead in frequent cases to the onset of ejaculation before or shortly after vaginal penetration, or an inability to keep erection or control ejaculation for a sufficient amount of time for a partner's sexual pleasure.

According to recent statistics in Korea, approximately 30–50% of adult males suffer from these sexual dysfunctions resulting from hypersensitivity of sexual stimulation, which leads to domestic discord in relationships and loss of self-confidence.

Generally, hypersensitivity of sexual stimulation is caused by a malfunction of the central nervous system due to chronic fatigue of the neurotransmitter system, hypersensitivity of the urinary duct or the glans receptor, endocrinal disorders, psychological causes, and the like. However, it was recently deduced that since the above-mentioned causes may react on the nerve system in simultaneous and complex manner, or a cooperation system between the central sexual nerve system in a man may be disrupted, a reflective ejaculation can easily be caused.

Hypersensitivity of sexual stimulation has been treated by psychotherapy and drug therapy. The psychotherapy involves long-term sexual behavioral counseling therapy provided by a specialized therapist to both the patient and his partner. However, such long-term treatment programs are complicated, expensive, can be uncomfortable for the patient and/or his partner, and have a poor success rate of less than 50%.

Drug therapy has been used more widely than psychotherapy because of the prompt therapeutic effect. Available drugs include psychotropic agents which suppress excitation of the sexual nerve system, such as antidepressants, and topical anesthetic agents which desensitizes the sexual peripheral nerve to delay ejaculation. However, the central nerve depressants likely make it impossible to have sexual relationships due to a loss of sexual desire, and the topical anesthetic agents, such as lidocaine ointment or spray, are not preferred because they should be applied just before intercourse due to their short duration. Therefore, sexual dysfunctions resulting from hypersensitivity of sexual stimulation cannot be effectively treated with drugs.

Korean Patent No. 148511 discloses a preventive and therapeutic pharmaceutical formulation for hypersensitivity of sexual stimulation, which essentially contain ginseng, dang-gui(Angelicae Gigantis Radix), yuk-jong-yong (Cistanchis Herba), cinnamon(Cinnamomi Cortex), sesin (Asiasari Radix), and sumsoo (Bufonis Venenum). The effect of this formulation on hypersensitivity of sexual stimulation has been proven through animal and clinical tests, and it is commercially available for external application.

However, since the formulation contains essential oils of herbal components, such as dang-gui, cinnamon, sesin, etc., the scent of the herbal components is so strong that it smells even after washing with soap, thereby limiting the use of the formulation. Also, the formulation is prepared from the crude extracts of essential herbal components, including dang-gui, ginseng, sumsoo, yuk-jong-yong, cinammon, sesin, etc., without purification. Accordingly, the product appears an unpleasant unique dark brown color from the extracts of herbal components and may contaminate underwear. Thus, it is difficult for a patient to conceal the application of the therapeutic formulation from his partner. Further, application of the formulation is inconvenient because it takes 30 minutes to 1 hour for the local anesthetic to take effect. Moreover, since the crude sumsoo extract is used without purification, non-pharmacological substances for hypersensitivity of sexual stimulation in the unpurified sumsoo extract, such as epinephrine and serotonin, may result in various side effects, such as penile smooth muscle contraction and impotence.

WO 0147539A1, pharmaceutical composition for preventing and treating erectile impotence using purified sumsoo extract, discloses sumsoo extraction and purification methods for preparing a pharmaceutical composition containing only Bufadienolides, excluding catecholamines, such as epinephrine, and indolalkylamines, such as serotonine. The purified sumsoo extract effectively eliminates the side effects of sumsoo extract obtained using water or alcohol as an extraction solvent in Korean Patent No. 0148511, such as impotence, penile smooth muscle contraction, and pain.

However, Bufadienolides used as the pharmaceutical component for treating hypersensitivity of sexual stimulation have both topical anesthetic and penial smooth muscle contraction effects. Therefore, side effects such as impotence cannot be suppressed only with the purified sumsoo extract alone.

SUMMARY OF THE INVENTION

The invention provides a scent free, colorless composition for the prevention and treatment of premature ejaculation and/or hypersensitivity of sexual stimulation, which includes purified sumsoo (Bufonis Venenum) extract and purified ginseng extract containing saponin as the main component, excluding any herbal essential oil component, and minimize side effects such as impotence and burning.

The composition for the prevention and/or treatment of premature ejaculation and/or hypersensitivity of sexual stimulation according to the present invention includes the purified sumsoo extract and the purified ginseng extract containing saponin as the main component, excluding any herbal essential oil component, wherein the penial smooth muscle contraction effect of Bufadienolides, which are known as pharmacological components of sumsoo, is suppressed.

Bufadienolides, the pharmacological components in the sumsoo extract, adversely cause contraction of the penial smooth muscle and in turn cause impotence. However, according to the present invention, the penial smooth muscle contraction effect is markedly reduced by mixing the sumsoo extract with the purified ginseng extract containing saponin as the main component.

According to the present invention, herbal essential oil components, such as dang-gui, yuk-jong-yong, cinnamon, etc., which appear unpleasant dark brown and smell strong, are excluded. The combination of the purified sumsoo extract and the purified ginseng extract containing saponin as the main component is proven to be an effective treatment for hypersensitivity of sexual stimulation. It is believed that the inhibition of smooth muscle contraction is by the saponin component of the purified ginseng extract.

The sumsoo extract used in the composition for the treatment of hypersensitivity of sexual stimulation according to the present invention is obtained by using, preferably, ethylacetate, dichloromethane, or chloroform, as an extraction solvent.

Extracting the sumsoo using at least one solvent selected from the group consisting of ethylacetate, dichloromethane and chloroform may be followed by an additional purification, for example, solvent fractionation or chromatography.

The pharmaceutical composition according to the present invention contains 0.01–3% by weight of the sumsoo extract and 0.01–5% by weight of the ginseng extract, based on the total weight of the composition. Preferably, the pharmaceutical composition according to the present invention contains 0.05–0.2% by weight the sumsoo extract and 0.1–0.2% by weight the ginseng extract, based on the total weight of the composition.

The ginseng extract used in the therapeutic composition for hypersensitivity of sexual stimulation according to the present invention is prepared by extracting a crude ginseng extract from raw ginseng using ethanol and purifying the crude ginseng extract by solvent fractionation with diethylether and butanol.

The pharmaceutical composition according to the present invention may be produced in any form suitable for application, for example, ointment, solution, suspension, gel, dispersion or the like, with gel form being preferred.

In the pharmaceutical composition according to the present invention, the amount of the extract in the final composition is reduced to $1/50^{th}$ or less of the amount of the crude extract used in the same volume of the conventional composition of Korean Patent No. 148511. Accordingly, percutaneous absorption inhancers, for example, Lauroglycol (Propylene Glycol Monolaurate), Pharmasolve (N-Methyl-2-Pyrrolidone), Transcutol (Diethylene Glycol Monoethyl Ether), carbomer, etc, which cannot be used in the conventional composition due to insolubility problems, can be further incorporated into the pharmaceutical composition according to the present invention. Compared with the conventional composition which takes effect 30 minutes to 1 hour after application, the pharmaceutical composition according to the present invention takes effect within about 5 minutes after application, and thus is convenient to use.

DETAILED DESCRIPTION OF THE INVENTION

Figures 1, 2:
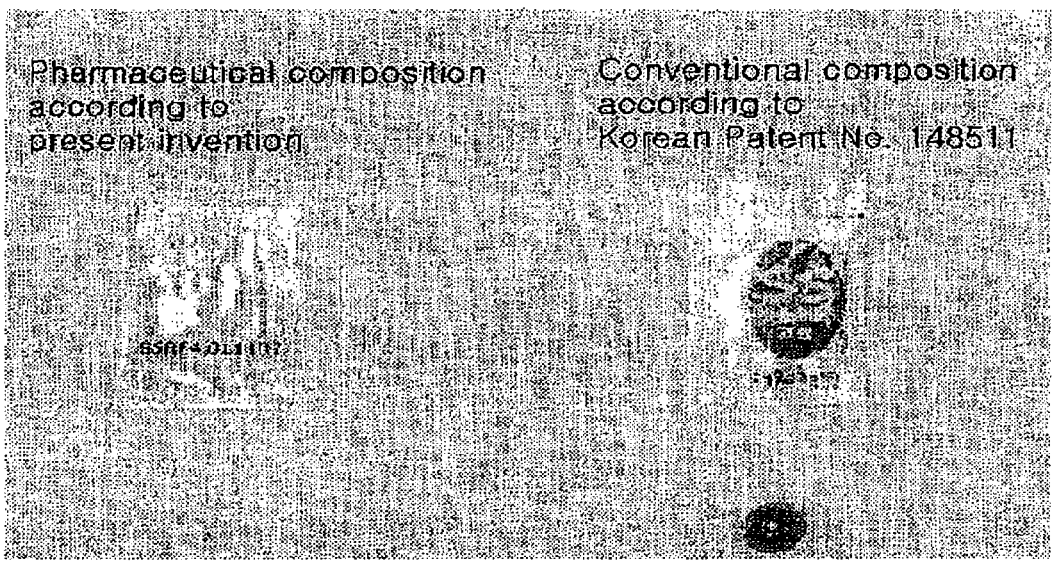
FIG. 1 shows the appearance of a conventional composition for the prevention and treatment of premature ejaculation and hypersensitivity of sexual stimulation.
FIG. 2 shows the appearance of a pharmaceutical composition for the prevention and treatment of premature ejaculation and hypersensitivity of sexual stimulation according to the present invention.

The present invention will be described in greater detail with reference to the following examples. The following examples are for illustrative purposes and are not intended to limit the scope of the invention.

EXAMPLE 1

(a) 2000 mL of ethylacetate was added to 400 g of sumsoo powder, and the mixture was subject to hot extraction in a water bath equipped with a reflux condenser at 70° C. for 4 hours and filtered. An equal amount of ethyleacetate was added to the filter cake and was again subject to extraction. The filtrate was combined with the previously obtained filtrate, concentrated under a reduced pressure, and dried to yield 62 g of dry extract.

(b) 1.5 g of the brown sumsoo-ethyleacetate extract obtained in step (a) was loaded onto a silicagel column, which was packed with 12 g of silicagel particles of 230–400 mesh, followed by elution with a solvent mixture of normal hexane and ethyleacetate. Through a rabbit corneal reflex test using each fraction of the eluent, each eluate fraction was subjected to a rabbit corneal reflex test and 1.1 g of colorless efficacious fractions having a topical anesthetic effect were collected.

(c) 500 mL of ethanol was added to 50 g of ginseng powder. The mixture was subject to hot extraction at 80° C. for 4 hours, twice, in a water bath equipped with a reflux condenser and filtered to obtain 8 g of crude ginseng extract. The crude ginseng extract was dissolved in 100 mL of distilled water, followed by shaking extraction, twice, with an addition of the equal amount of diethylether, to separate an aqueous fraction. The aqueous fraction was subject to shaking extraction, twice, with the addition of 100 mL of butanol hydrate, and the resulting butanol fraction was concentrated under a reduced pressure to yield 4.5 g of ginseng extract powder, which was partially purified and containing saponin as the main component.

(d) 130 trig of the sumsoo extract powder prepared in step (b) and 150 rug of the ginseng extract powder prepared in step (c) were mixed thoroughly with a base composition consisting of Lauroglycol (Propylene Glycol Monolaurate), Pharmasolve (N-Methyl-2-Pyrrolidone), Transcutol (Diethylene Glycol Monoethyl Ether), and carbomer to obtain 100 g of colorless, odorless gel composition.

EXPERIMENTAL EXAMPLE 1

Topical Anesthetic Effect Verification Through Rabbit Corneal Reflex Test

The topical anesthetic effect of the pharmaceutical composition prepared in Example 1 was confirmed through a rabbit corneal reflex test.

Three adult male rabbits were bound up, and a lower eyelid of each rabbit was stretched away from the eyeball and fixed without anesthetization. 0.1 mL of the composition prepared in Example 1 was applied into the eye, and the eyelid was shut for about 1 minute to prevent loss of the composition. The corneal was irritated with a brush ten times after 5 minutes, 10 minutes, 20 minutes, and 30 minutes from application, and the number of resulting corneal reflexes was recorded. An incomplete shutting of the eyelid or a slow corneal reflex was counted as a half of a reflex. The same corneal reflex test was carried out using 0.1 mL of the base composition for comparison.

The results of the rabbit corneal reflex test are shown in Table 1.

TABLE 1

Rabbit corneal reflex test results

| Sample | The number of subject animals | Average number of corneal reflexes | | | |
|---|---|---|---|---|---|
| | | 5 min | 10 min | 20 min | 30 min |
| Control group | 3 | 9.0 | 9.3 | 8.7 | 9.0 |
| Present invention | 3 | 0.7 | 0.3 | 1.3 | 1.7 |

As is apparent from the results of the rabbit corneal reflex test for topical anesthetic effect evaluation in Table 1, the pharmaceutical composition according to the present invention significantly suppressed the corneal reflex providing a good topical anesthetic effect, compared to the control group to which only the base composition was applied.

EXPERIMENTAL EXAMPLE 2

Anti-impotence Effect Verification Through Rabbit Penile Cavernous Smooth Muscle Tissue Contraction Test Rabbits were anesthetized by intravenously injecting pentobarbital via ear vein and killed by bleeding. The penis was isolated from the rabbits and immersed in Tyrode's solution, and the penile cavernous tissue was isolated just before the test. The connective tissue and surrounding muscles of the penis were removed and the tissue membrane was incised using a surgical knife to isolate the pure penile cavernous tissue.

The isolated penile cavernous tissue was trimmed into 2×2×6 mm segments. One end of each tissue segment was fixed to the bottom of an organ bath containing a Tyrode's solution while the other end was bound to a force displacement transducer to record the contraction of the penile tissue segment on a polygraph. During the test, warm water was circulated through the double-jacketed walls of the organ bath so as to keep the Tyrode's solution at a temperature of 37° C., and a gas mixture of 95% oxygen and 5% carbon dioxide was continuously supplied so as to keep the Tyrode's solution at pH 7.4. The initial tension applied was increased by a force corresponding to 0.5 g every 30 minutes over 1–2 hours up to a force of 2 g, and the tension of the penile cavernous tissue at pause was maintained under the force of 2 g for stabilization. The stabilized penile cavernous tissue was treated using 0.1 mL of sumsoo extract solution in ethanol at a concentration of 0.02 mg/mL, wherein the sumsoo extract was obtained in step (b) of Example 1. When the penile cavernous tissue was contracted to a maximum level in the polygraph, 1 mL of ginseng extract solution, wherein the ginseng extract was obtained in step (c) of Example 1, in ethanol at concentrations of 0.25 mg/mL, 0.5 mg/mL, 1.0 mg/mL, and 2.0 mg/mL was applied to the contracted tissue. Then, the contraction force of the cavernous smooth muscle tissue to which ginseng extract solution was applied was measured and compared with the control to which ginseng extract solution was not applied. The smooth muscle contraction inhibitory ratio was calculated for the tissues to which the ginseng extract solutions were applied. The results are shown in Table 2.

TABLE 2

Results of the rabbit penile cavernous smooth muscle contraction test

| Concentration of ginseng extract solution (mg/ml) | Smooth muscle contraction inhibitory ratio (%) |
|---|---|
| 0 | — |
| 0.25 | 22.4 ± 2.5** |
| 0.5 | 48.1 ± 8.5** |
| 1.0 | 62.3 ± 8.1** |
| 2.0 | 100** |

**significant at $p < 0.01$

As can be seen in Table 2, compared with the control using the sumsoo extract alone, when the sumsoo extract and the ginseng extract were used together, the smooth muscle contraction was relieved in proportion to the concentration of the ginseng extract. Therefore, it was evident that the addition of the ginseng extract to the sumsoo extract had an effect of relieving reduced erectile response caused by the penile smooth muscle contraction.

EXPERIMENTAL EXAMPLE 3

Color and Odor Evaluation

The color, viscosity, and odor of the pharmaceutical composition according to the present invention was evaluated comparitively with the conventional composition disclosed in Korean Patent No. 0148511, which is commercially available under the brand name "SS cream™."

The appearances of the pharmaceutical composition according to the present invention and the conventional SS cream™ are shown in FIGS. 1 and 2.

As shown in FIG. 1, the SS cream™ is dark brown, whereas the composition according to the present invention is colorless as shown in FIG. 2. The SS cream™ has strong herbal odor, whereas the composition according to the present invention is odorless. The SS cream™ is a solution with low fluidity, whereas the composition according to the present invention is a thick gel. Therefore, the pharmaceutical composition according to the present invention is determined to be very convenient to use in terms of color, odor, and viscosity.

EXPERIMENTAL EXAMPLE 4

Primary Clinical Test

The therapeutic effect of the gel composition prepared in Example 1 for hypersensitivity of sexual stimulation was tested using 35 male volunteers suffering from hypersensitivity of sexual stimulation. The subjects were instructed to uniformly apply 0.2 g of the gel composition prepared in Example 1 to the penis glans, wash it off about 5 minutes later, and have sexual intercourse after 1 hour from the washing. Later, the subjects were asked how much longer the sexual intercourse lasted compared to their normal duration. The results are shown in Table 3.

TABLE 3

Prolonged sexual intercourse duration effect

| Prolonged sexual intercourse duration | The number of subjects | Ratio (%) |
|---|---|---|
| 15 min or longer | 9 | 25.7 |
| 10–15 min | 15 | 42.8 |
| 2–10 min | 9 | 25.7 |
| 2 min or less | 2 | 5.7 |

As can be seen in Table 3, 94% of the test subjects (33 of the 35 subjects) were greatly satisfied with the extension of sexual intercourse, and about 26% (9 of the 35 subjects) reported an extension of 15 min or longer. Only two subjects complained of reduced erectile response due to penile muscle contraction. Evidently, the composition according to the present invention exhibits reduced side effects.

INDUSTRIAL APPLICATION

As described above, the pharmaceutical composition for the prevention and treatment of premature ejaculation and hypersensitivity of sexual stimulation according to the present invention is convenient to use, has reduced side effects, such as reduction of erectile response, extends sexual intercourse and leads to a satisfactory sexual life by enhancing sexual performance.

What is claimed is:

1. A pharmaceutical composition for the prevention and treatment of premature ejaculation and/or hypersensitivity of sexual stimulation, the pharmaceutical composition comprising an herbal component, wherein the herbal component consists of purified sumsoo extract and purified ginseng extract containing saponin,
    wherein the purified sumsoo extract is obtained by using at least one solvent selected from the group consisting of ethylacetate, dichloromethane, and chloroform as an extraction solvent; and
    wherein the purified ginseng extract is obtained through solvent fractionation or column chromatography after being extracted using ethanol.

2. The pharmaceutical composition of claim 1, wherein the purified sumsoo extract is contained in an amount of 0.01–3% by weight and the purified ginseng extract is contained in an amount of 0.01–5% by weight based on the total weight of the pharmaceutical composition.

3. The pharmaceutical composition of claim 1, further comprising a percutaneous absorption enhancer.

4. The pharmaceutical composition of claim 1, wherein the pharmaceutical composition is in gel form.

5. The pharmaceutical composition of claim 3, wherein the percutaneous absorption enhancer is selected from the group consisting of Propylene Glycol Monolaurate, N-Methyl-2-Pyrrolidone, Diethylene Glycol Monoethyl Ether, and a mixture of the forgoing substances.

* * * * *